United States Patent [19]

Ninomiya et al.

[11] Patent Number: 5,055,679
[45] Date of Patent: Oct. 8, 1991

[54] SURFACE ANALYSIS METHOD AND APPARATUS

[75] Inventors: Ken Ninomiya, Hachioji; Keizo Suzuki, Kodaira, both of Japan

[73] Assignee: Hitachi, Ltd., Tokyo, Japan

[21] Appl. No.: 460,373

[22] Filed: Jan. 3, 1990

[30] Foreign Application Priority Data

Jan. 6, 1989 [JP] Japan ................................. 64-303

[51] Int. Cl.$^5$ ............................................. H01J 37/00
[52] U.S. Cl. .................................. 250/306; 250/307; 250/310
[58] Field of Search ................ 250/306, 307, 310, 397

[56] References Cited

U.S. PATENT DOCUMENTS

| | | | |
|---|---|---|---|
| 3,814,943 | 6/1974 | Baker et al. | 356/71 |
| 3,971,939 | 7/1976 | Hoppe | 250/311 |
| 4,499,540 | 2/1985 | Kowalski | 378/58 |
| 4,679,946 | 7/1987 | Rosencwaig et al. | 356/445 |
| 4,758,723 | 7/1988 | Wardell et al. | 250/305 |
| 4,788,495 | 11/1988 | Plies | 250/311 |

FOREIGN PATENT DOCUMENTS 61-292600 6/1985 Japan .
62-265555 11/1987 Japan .

OTHER PUBLICATIONS

"Fundamentals of X-Ray Photo Emission Spectroscopy", Grunthaner, *MRS Bulletin,* 30, Sep. 1987, pp. 60-64.
"Photoelectron Spectromicroscopy", Beamson et al., *Nature,* vol. 290, Apr. 1981.

*Primary Examiner*—Bruce C. Anderson
*Attorney, Agent, or Firm*—Antonelli, Terry, Stout & Kraus

[57] ABSTRACT

A method of and an apparatus for analyzing a surface are disclosed, in which the intensity profile of a probe beam at the surface of a sample is measured, the intensity distribution of a detection signal along the surface of the sample is measured by scanning the surface of the sample with the probe beam, and mathematical transformation is carried out for each of the measured intensity profile and the measured signal-intensity distribution, to make surface analysis with high resolution.

34 Claims, 5 Drawing Sheets

SURFACE ANALYSIS METHOD AND APPARATUS

BACKGROUND OF THE INVENTION

The present invention relates to a novel surface analysis technique, and more particularly to a method of and an apparatus for analyzing a small area of a sample surface with high resolution.

In the field of surface analysis, the size of an analyzed area has been greatly reduced in recent years for the following reason. That is, as seen in a process for fabricating a recent semiconductor device, each of elements making up the semiconductor device becomes small in size, the thickness of the film used is reduced, and a composite material is frequently used. Accordingly, it is required to know the material property, structure and electrical characteristic of a very small surface area. Further, it is judged from the pattern size used in the semiconductor device and the size of grain boundary in the material used that a surface area to be analyzed has a diameter of 1 μm or less. Accordingly, a lateral resolution required in the surface analysis technique (that is, the linear dimension of a minimum surface area which can be analyzed is less than or equal to 1 μm.

In conventional surface analysis techniques, the following methods have been used for increasing the lateral resolution.

One of the methods is to focus a probe beam on a sample surface to be analyzed, by means of an optical element capable of focusing a light beam, an electron lens system, or an ion lens system. Typical examples of the method are seen in an electron microscope and an apparatus for μ-ESCA (F. J. Grunthaner, MRS Bulletin, Vol. 30, page 61, 1987). Further, an X-ray beam is focused by means of a total reflection mirror or a zone plate (Japanese Patent Applications JP-A-61-292,600 and JP-A-62-265,555).

Another method for increasing the lateral resolution is to limit the field of a detection system without performing any operation for the probe beam. In this method, an electron lens system, an aperture and a strong magnetic field are used for the above limitation. For example, in the above apparatus for μ-ESCA, not only soft X-rays for forming the probe beam are focused, but also an electron lens system and an aperture are used for photoelectrons, to improve the lateral resolution. Further, in a different apparatus for μ-ESCA, a strong magnetic field is generated in the vicinity of a sample surface, to capture photoelectrons from the sample surface by the magnetic field through an electron cyclotron motion, thereby improving the lateral resolution (G. Beamson et al., Nature, Vol. 290, page 556, 1981).

In these methods, however, there arise the following problems. The first problem is that, in order to focus a probe beam on an area having a diameter of 1 μm or less, it is necessary to develop an optical system with the smallest aberration. A technique with a high precision machining, required for developing the optical system, and it is very difficult to realize the optical system. In fact, an ion beam spot and an X-ray beam spot each having a diameter of 1 μm or less have not yet been realized, though an electron beam can form such a beam spot.

The second problem relates to the method of the field limited type. It is impossible to greatly improve the lateral resolution of surface analysis by this method. The reason for this will be explained below. Now, let us consider a case where electrons emitted from a sample surface are observed for surface analysis. When the sample surface is irradiated with a probe beam, electrons having a variety of kinetic energies are emitted from the sample surface in all directions. Variations in ejection angle and kinetic energy of electron result in the aberration of a lens system for detecting the electrons. In order to increase the resolution of surface analysis, it is necessary to make the aberration as small as possible. The above aberration, however, is inevitable in electron emission, and it is impossible to eliminate the aberration.

As mentioned above, in the conventional methods for improving the resolution of surface analysis, there arise problems that it is technically difficult to focus a probe beam on a very small area, and the methods are essentially undesirable.

SUMMARY OF THE INVENTION

It is an object of the present invention to provide a method of and an apparatus for analyzing a small area of a surface with high lateral resolution.

In order to attain the above object, according to the present invention, the intensity profile of a probe beam and the signal distribution which is obtained by scanning a sample surface with the probe beam, are both measured, and mathematical transformation is carried out for the intensity profile and the signal distribution, to obtain the analytical result for the sample surface. When surface analysis is made in the above manner, the lateral resolution of the surface analysis is greatly improved. In a conventional method of analyzing a sample surface by irradiating the sample surface with a focused probe beam, the lateral resolution of surface analysis is determined by the diameter of the focused probe beam. According to the present invention, lateral resolution which is far higher than the lateral resolution determined by the beam diameter, can be obtained.

In the present invention, a probe beam includes a light beam and a particle beam. A light beam includes not only an ordinary light beam (for example, an ultraviolet light beam, a visible light beam, an infrared light beam) and a laser beam but also an electromagnetic beam (for example, an X-ray beam, a synchrotron radiation light beam). A particle beam includes a charged particle beam (for example, an electron beam, an ion beam) and a neutral particle beam.

Now, mathematical transformation (for example, integral transformation) used in the present invention will be explained below.

Let us express the distribution of an element A in a sample surface by $n_A(x,y)$. The distribution of the element A in the direction of thickness will not be considered in the following explanation for the sake of simplicity. However, the following explanation will essentially hold for a case where the element A is non-uniformly distributed in the direction of thickness. The lateral resolution of surface analysis is dependent upon how precisely the distribution $n_A(x,y)$ is determined. Further, let us express the intensity profile of a probe beam at the sample surface by $f(\eta,\theta)$. When the probe beam impinges on the sample surface so that the center axis of the probe beam is placed at a position $(x_o,y_o)$ on the sample surface, and a signal S due to the element A is detected by a detector, we can obtain the following equation:

$$S(x_o,y_o) = K \cdot F_\Omega \int \int n_A(x_o+\eta, y_o+\theta) f(\eta,\theta) d\eta d\theta \quad (1)$$

where K is a constant independent of integration, F indicates the total intensity of incident beam, $\Omega$ is the area of integration (that is, a surface area irradiated with the probe beam), and $f(\eta,\theta)$ is a function defined by an equation $\Omega \int \int f(\eta,\theta) d\eta d\theta = 1$.

As mentioned above, in the equation (1), the function $f(\eta,\theta)$ is defined within the area $\Omega$. Now, let us define the function $f(\eta,\theta)$ on the outside of the area $\Omega$ in the following manner:

$$f(\eta,\zeta) = \begin{cases} f(\eta,\zeta) & ; (\eta,\zeta)\epsilon\Omega \\ 0 & ; (\eta,\zeta)\epsilon\Omega \end{cases} \quad (2)$$

When Fourier transformation is carried out for the equation (1) using the equation (2), we can obtain the following equation:

$$S(X,Y) = K \cdot F \cdot 2\pi N_A(X,Y) \overline{F}(X,Y) \quad (3)$$

where $$N_A(X,Y) = \frac{1}{2\pi} \int_{-\infty}^{\infty} \int n_A(x,y) e^{-i(xX+yY)} dx dy \quad (4)$$

$$\overline{F}(X,Y) = \frac{1}{2\pi} \int_{-\infty}^{\infty} \int f(x,y) e^{-i(xX+yY)} dx dy \quad (5)$$

From the equations (3) and (4), the distribution $n_A(x,y)$ can be obtained as follows.

$$n_A(x,y) = \frac{1}{K \cdot F} \frac{1}{(2\pi)^2} \int_{-\infty}^{\infty} \int \frac{S(X,Y)}{\overline{F}(X,Y)} e^{-i(xX+yY)} dXdY \quad (6)$$

As can be seen from the equation (1), a function $S(X,Y)$ is a Fourier transform of the detection signal corresponding to each point on the sample surface. While, a function $\overline{F}(X,Y)$ is obtained by carrying out Fourier transformation for the intensity profile $f(\eta,\theta)$ of the probe beam. As is evident from the equation (6), the distribution $n_A(x,y)$ can be calculated from the quantities $S(X,Y)$ and $\overline{F}(X,Y)$ which have been calculated from measured quantities $S(x_o,y_o)$ and $f(\eta,\theta)$.

A positional interval, at which the value of $n_A(x,y)$ is determined, (that is, the lateral resolution of surface analysis) is nearly the same as a positional interval, at which the value of each of the functions $S(X,Y)$ and $\overline{F}(X,Y)$ is determined (that is a positional interval, at which the value of each of the signal $S(x_o,y_o)$ and the intensity profile $f(\eta,\theta)$ is determined). The signal $S(x_o,y_o)$ and the intensity profile $f(\eta,\theta)$ can be measured at an interval which is far smaller than the diameter of the probe beam. Consequently, even when the probe beam having a large diameter is used, the lateral resolution of surface analysis can be increased. Further, in a case where the probe beam having a small diameter (that is, focused probe beam) is used, the lateral resolution of surface analysis is further improved. As is evident from the above explanation, the surface analysis according to the present invention is entirely different from conventional surface analysis, in which the lateral resolution is determined by the diameter of the probe beam. Further, the equations (1) to (6) hold for any probe beam. Accordingly, the present invention is applicable to all of surface analysis methods using a probe beam.

Further, the present invention is effective even in a case where the value of the function $f(\eta,\theta)$ varies with the variable $\eta$ and $\theta$ in a complicated manner. Now, let us consider a case where the function $f(\eta,\theta)$ has a plurality of maximum values when the value of $\eta$ is changed while keeping the value of $\theta$ constant, by way of example. In this case, according to the conventional surface analysis method, the lateral resolution is determined by the diameter of the whole probe beam (for example, the full width at the half maximum of the intensity profile $f(\eta,\theta)$. While, according to the present invention, the lateral resolution is determined by, for example, the full width at half maximum of a peak corresponding to one of the maximum values. Accordingly, even in the above case, the present invention can realize higher resolution than the resolution in the conventional method.

In the above, a case where Fourier transformation is used as the integral transformation, has been explained, by way of example. It is needless to say that integral transformation other than the Fourier transformation can be used.

DESCRIPTION OF THE PREFERRED EMBODIMENTS

Embodiments of the present invention will be explained below in detail.

EMBODIMENT-1

Figure 1:
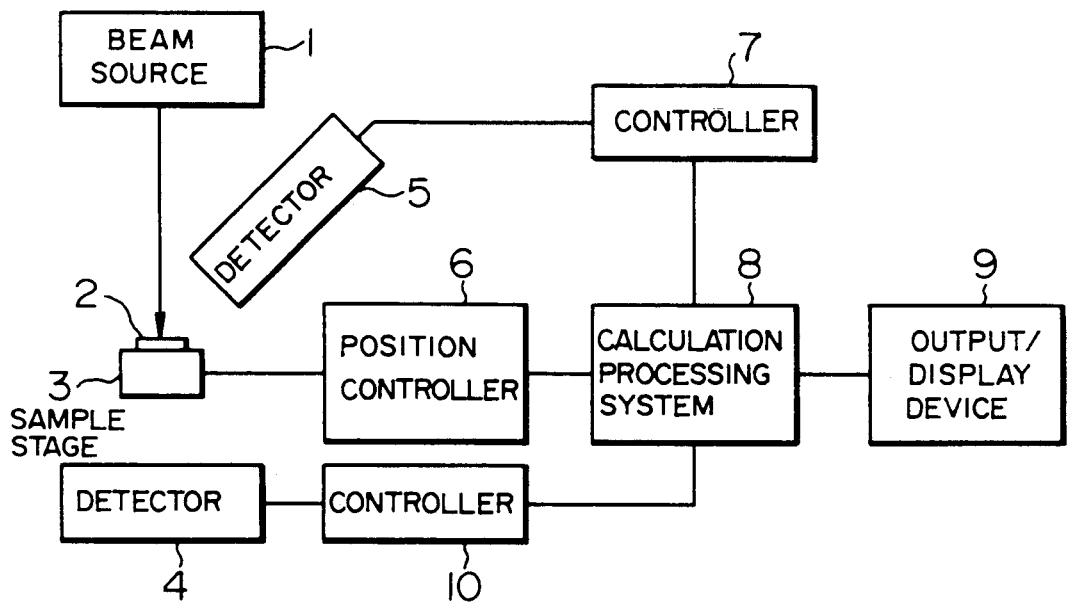
FIGS. 1 to 8 are block diagrams showing embodiments of an apparatus for analyzing a surface in accordance with the present invention.

FIG. 1 shows the first embodiment of an apparatus for analyzing a surface in accordance with the present invention. Referring to FIG. 1, a probe beam (or probe particles) emitted from a beam source 1 impinge on the surface of a sample 2 placed on a sample stage 3. The beam source 1 is one of a charged particle source, a neutral particle source, and a light source for generating radiations such as X-rays, a synchrotron radiation and a laser beam. The electrons, ions, neutral particles and light each emitted from that surface of the sample 2 which is irradiated with the probe beam, are detected by a detector 5. The detector 5 is one of a detector capable of performing energy analysis (for example, a static energy analyzer, an energy dispersive analyzer, or a wavelength dispersive X-ray detector), a detector capable of making mass analysis (for example, a mass spectrometer), and a detector for merely detecting electrons, ions, neutral particles, or light. In other words, detectors of various kinds and detectors having various performance can be used as the detector 5. The detector 5 is controlled by a controller 7.

While, a detector 4 for measuring the intensity profile of the probe beam is positioned in the rear of the sample 2. The intensity profile of the probe beam is two-dimensional distribution, as indicated by the equation (2). Accordingly, it is preferable to use a two-dimensional detector as the detector 4. In a case where the two-dimensional detector is not used, the detector 4 is used with a knife edge (shown in FIG. 2), a pin hole, or a slit. Like the detector 5, the detector 4 detects electrons, ions, neutral particles, or light. When the intensity profile of the probe beam is measured, the sample 2 and the sample stage 3 are moved so as not to hinder the probe beam, and the detector 4 is raised to a position corresponding to the measured sample surface, if necessary.

The sample stage 3 can make three-dimensional fine displacement and the fine displacement is carried out with the aid of a piezoelectric device. The fine displacement of the sample stage 3 is controlled by a position controller 6.

Next, explanation will be made of a signal/data processing system. An observed or detected signal from the detector 5 is inputted to a high speed calculation processing system 8, which is formed of a high speed processor provided with a large memory and display means. Further, a signal from the position controller 6 for indicating the probe beam position on the sample surface which is irradiated with the probe beam, is inputted to the calculation processing system 8. Thus, the function $S(X,Y)$ of the equation (3) can be determined from these signals. While, the output signal of the detector 4 is transferred to the calculation processing system 8 through a controller 10 for the detector 4. It is supposed in the following processing that the detector 4 is a two-dimensional detector (otherwise, processing in EMBODIMENT-2 will be carried out). The output signal of the controller 10 corresponds to the function $f(x,y)$ of the equation (5). The calculation processing system 8 calculates the function $\overline{F}(X,Y)$ from the function $f(x,y)$ at high speed by using the equation (5). The measurement of the intensity profile $f(x,y)$ and the calculation of the function $\overline{F}(X,Y)$ is carried out prior to the measurement and calculation for obtaining the function $S(X,Y)$.

The calculation processing system 8 calculates the distribution $n_A(x,y)$ from the functions $S(X,Y)$ and $\overline{F}(X,Y)$, by using the equation (6). The result thus obtained is displayed on a display screen of the display means included in the calculation processing system 8. Further, the above result can be displayed on a display screen of a separate output/display device 9. Thus, the result of surface analysis can be displayed in the form of, for example, a picture image.

According to the present embodiment, the distribution of a to-be-detected substance on a sample surface can be determined from the intensity profile of a probe beam and the distribution of detected signal along the sample surface, through mathematical transformation. Accordingly, even when the probe beam has a large diameter, surface analysis can be made with high resolution.

EMBODIMENT-2

Figure 2:
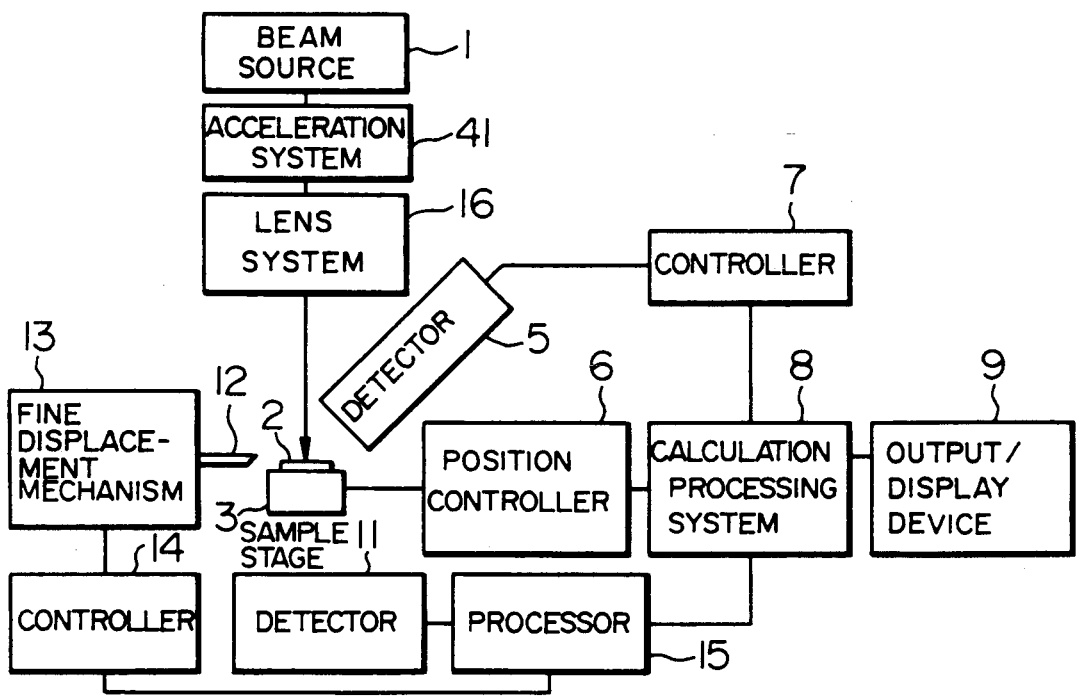

In the embodiment of FIG. 1, an optical system for focusing the probe beam is not located between the beam source 1 and the sample 2. When a small size probe beam is used, surface analysis can be made with high reliability and high resolution. In order to realize the high-resolution surface analysis with the high-reliability, the probe beam (or probe particles) emitted from the beam source 1 are focused on the sample surface, and the above-mentioned mathematical transformation is carried out. FIG. 2 shows the second embodiment of an apparatus for analyzing a surface in accordance with the present invention which embodiment employs a focused probe beam.

Referring to FIG. 2, the probe beam (or probe particles) emitted from the beam source 1 are focused on the surface of the sample 2 by a lens system 16. The lens system 16 is one of an electric lens system and an optical lens system including a reflecting mirror system. The lens system 16 is selected in accordance with the kind of the probe beam (or probe particles). In a case where the acceleration of particles is not required for focusing the probe beam, for example, in a case where the probe beam is a light beam, an acceleration system 41 can be removed.

The intensity profile of the probe beam is measured by using a knife edge 12 and a detector 11. It is to be noted that in the first embodiment, the intensity profile is measured only by the detector 4 formed of a two-dimensional detector. The knife edge 12 may be replaced by a slit or pin hole.

The knife edge 12 is attached to a fine displacement mechanism 13 which is controlled by a controller 14. A signal delivered from the controller 14 for indicating the position of the knife edge 12 is transferred to a processor 15, together with the output signal of the detector 11. The processor 15 determines the intensity profile $f(x,y)$ from these signals, and the intensity profile thus obtained is inputted to the high speed calculation processing system 8. Other parts than the above-mentioned are the same as those shown in FIG. 1.

According to the present embodiment, the sample surface is irradiated with a very small size probe beam. Hence, surface analysis according to the present embodiment will be higher in reliability and resolution than surface analysis according to the first embodiment.

EMBODIMENT-3

Figure 3:
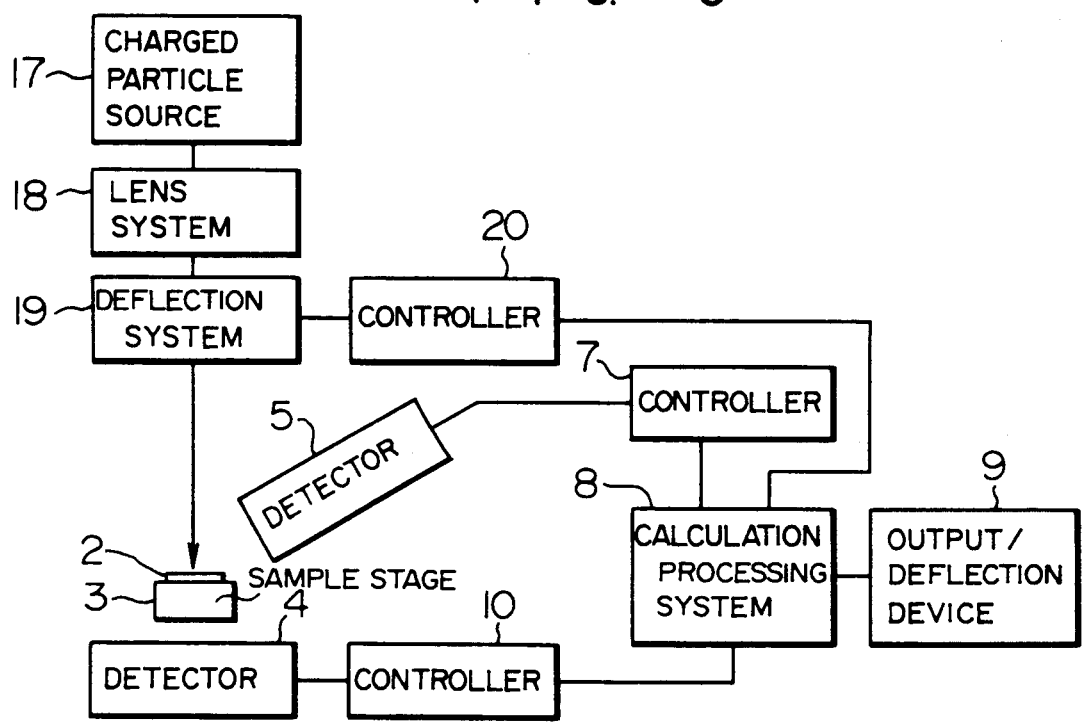

As has been already mentioned, in the present invention, it is necessary to measure the distribution of detected signal along a sample surface. In other words, it is required to scan the sample surface with the probe beam. In the first and second embodiments, this scanning operation is performed by the fine displacement of the sample stage 3. However, the sample surface can be scanned with the probe beam in a manner different from that in the first and second embodiments. FIG. 3 shows the third embodiment of an apparatus for analyzing a surface in accordance with the present invention, in which embodiment the surface is scanned with a probe beam in a manner different from that shown in FIGS. 1 and 2.

Referring to FIG. 3, the beam (or particles) from a charged particle source 17 are focused by a lens system 18, pass through a deflection system 19, and then impinge on the surface of the sample 2. The deflection system 15 is controlled by a controller 20 so that the surface of the sample 2 is scanned with the probe beam.

A signal indicating the scanning operation of the probe beam (that is, the position signal of the probe beam) is supplied from the controller 20 to the high speed calculation processing system 8. Further, the observed signal from the detector 5 is inputted to the calculation processing system 8 through the controller 7. The calculation processing system 8 determines the function $S(X,Y)$ from the position signal and the observed signal. Other parts than the above-mentioned are the same as those in the first and second embodiments.

EMBODIMENT-4

Figure 4:
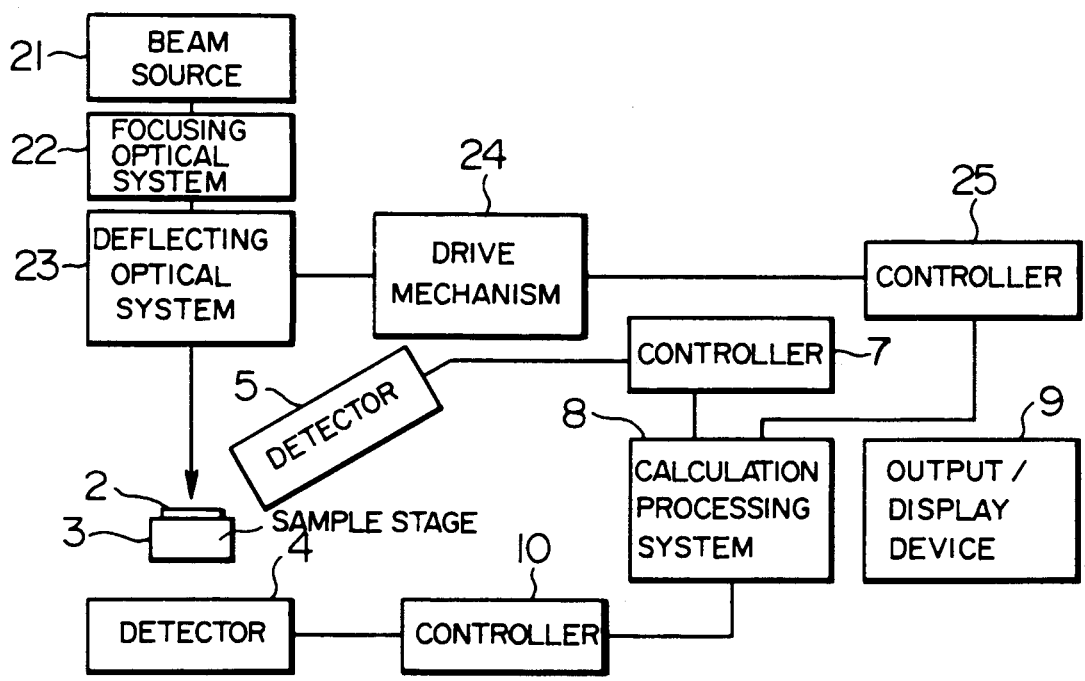

FIG. 4 shows the fourth embodiment of an apparatus for analyzing a surface in accordance with the present invention, in which embodiment a probe beam other than a charged particle beam is deflected so as to perform a scanning operation. Referring to FIG. 4, the probe beam (or probe particles) emitted from a beam source 21 are focused by an optical system 22, pass through an optical system 23 for deflections, and then impinge on the surface of the sample 2. The optical system 23 for deflection is controlled by a drive mechanism 24, which is controlled by a controller 25. In a case where a light beam is used as the probe beam, a reflection mirror can act as the optical system 23 for deflection. By using such a deflection system, the surface of the sample 2 can be scanned with the probe beam.

A signal indicating the scanning operation of the probe beam (that is, the position signal of the probe beam) is supplied from the controller 25 to the high speed calculation processing system 8. Further, the observed signal from the detector 5 is inputted to the calculation processing system 8 through the controller 7. The calculation processing system 8 determines the function S(X,Y) from the position signal and the observed signal. Other parts than the above-mentioned are the same as those in the first to third embodiments.

In the third and fourth embodiments, the deflection system 19 and the system 23 for deflection are located at the rear of the lens system 18 and the optical system 22, respectively. Alternatively, the systems 19 and 23 may be located in front of the systems 18 and 22, respectively.

EMBODIMENT-5

Figure 5:
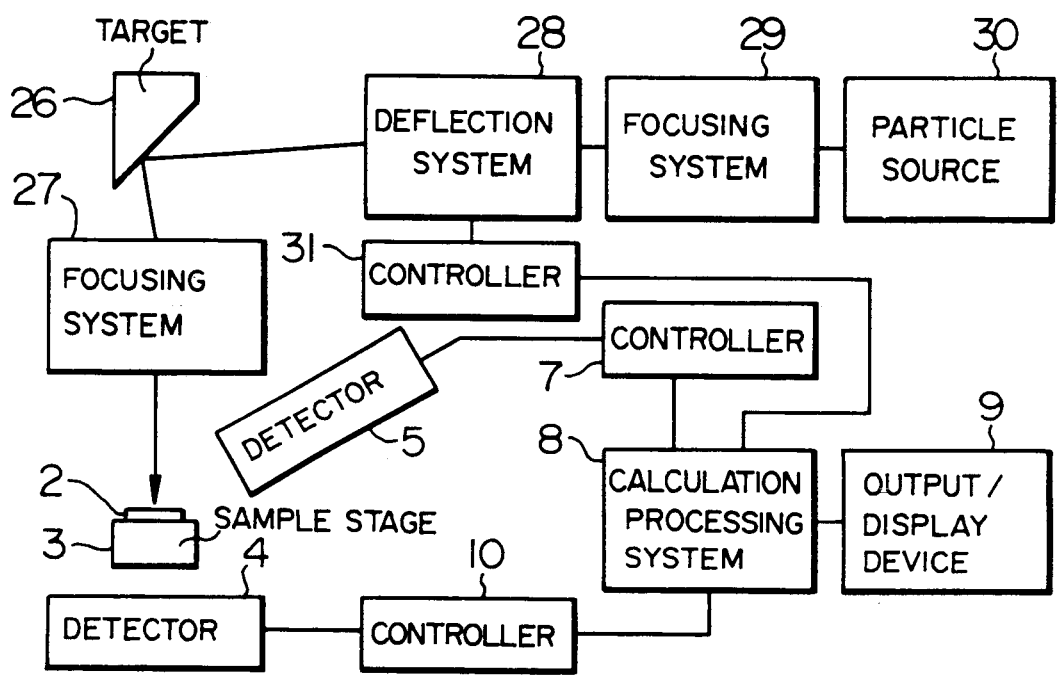

FIG. 5 shows the fifth embodiment of an apparatus for analyzing a surface in accordance with the present invention, in which embodiment a sample surface is scanned with the probe beam in a different manner. In the present embodiment, a position where the probe beam is generated, is changed to scan the sample surface with the probe beam. For example, in a case where a light beam is used as the probe beam, surface analysis can be made by the present embodiment.

Referring to FIG. 5, a beam (or particles) emitted from a particle source 30 pass through a focusing system 29, are deflected by a deflection system 28, and then impinge on a target 26. Probe particles which are emitted from the target 26 on the basis of the bombardment of the target with the particle beam, pass through another focusing system 27, and then impinge on the surface of the sample 2. The surface of the sample 2 can be scanned with the probe beam, by changing a position where the probe particles are generated.

A position where the probe particles are generated, is controlled by a controller 31 which is connected to the deflection system 28. Accordingly, the position of the probe beam on the surface of the sample 2 can be controlled by the controller 31. A signal corresponding to the position of the probe beam on the surface of the sample 2 is supplied from the controller 31 to the high speed calculation processing system 8, which determines the function S(X,Y) from the above signal and the output signal of the controller 7. Other parts than the above-mentioned are the same as those in the first to fourth embodiments.

The characteristic feature of the third to fifth embodiments resides in that the scanning speed is higher than that in a case where the sample stage 3 makes fine displacement. That is, the function S(X,Y) can be determined rapidly, as compared with a case where the sample stage 3 is moved.

EMBODIMENT-6

Figure 6:
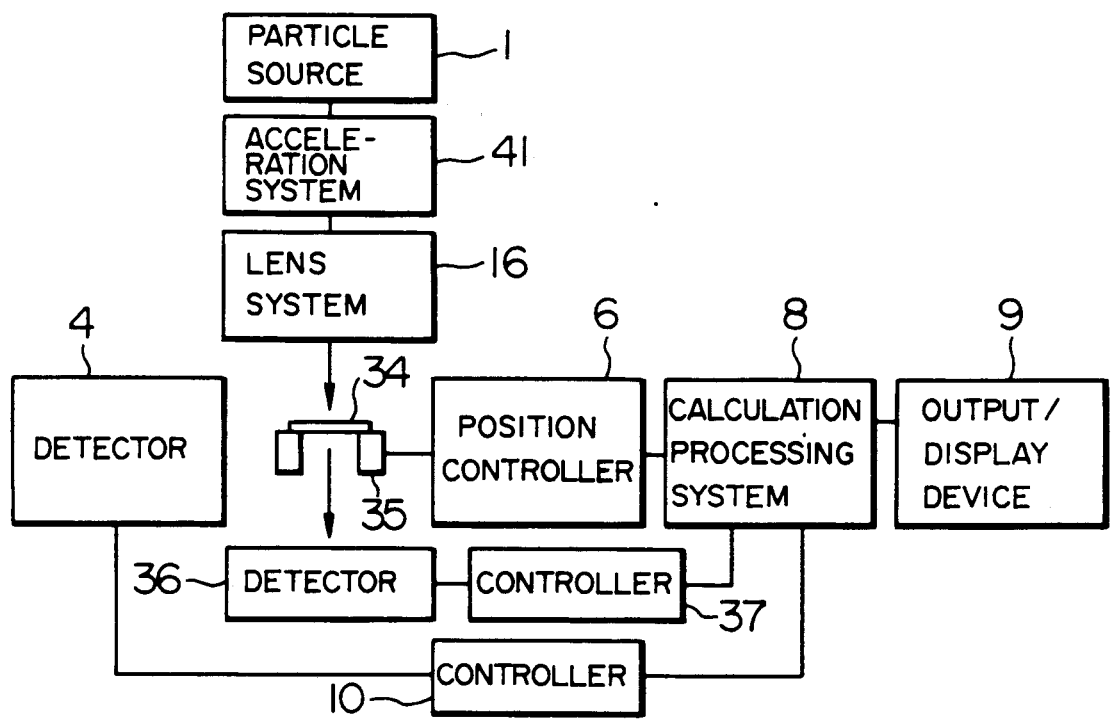

In the first to fifth embodiments, electrons, ions, neutral particles, or light is generated by irradiating the surface of the sample 2 with the probe beam, and observed for surface analysis. The method for obtaining a high-resolution according to the present invention is not limited to the emission from the surface, of the sample, but is applicable to other cases. FIG. 6 shows the sixth embodiment of an apparatus for analyzing a surface in accordance with the present invention, in which embodiment a phenomenon other than surface emission is utilized.

Referring to FIG. 6, a probe beam (or probe particles) emitted from the particle source 1 impinge on a sample 34. At this time, some of the particles included in the probe beam interact with atoms (or molecules) constituting the sample 34. Thus, the particle-energy distribution and the intensity of the probe beam having passed through the sample 34 are different from the particle-energy distribution and the intensity of the probe beam incident on the sample. Such a change in energy distribution and intensity is detected by a detector 36. Any device capable of detecting the particle-energy distribution and the intensity of the probe beam, can be used as the detector 36.

A detected signal from the detector 36 is inputted to the high speed calculation processing system 8 through a controller 37 for the detector 36. While, as in the first embodiment, a signal indicating the position of the probe beam is supplied from the controller 6 for controlling the fine displacement of the sample stage 35, to the high speed calculation processing system 8. Accordingly, the function S(X,Y), that is, the distribution of detected signal can be obtained from the above signals.

As in the first to fifth embodiments, the mathematical transformation is carried out by the high speed calculation processing system 8. Accordingly, the present embodiment can make surface analysis with high resolution, when a transmitted beam is used for the surface analysis.

EMBODIMENT-7

Figure 7:
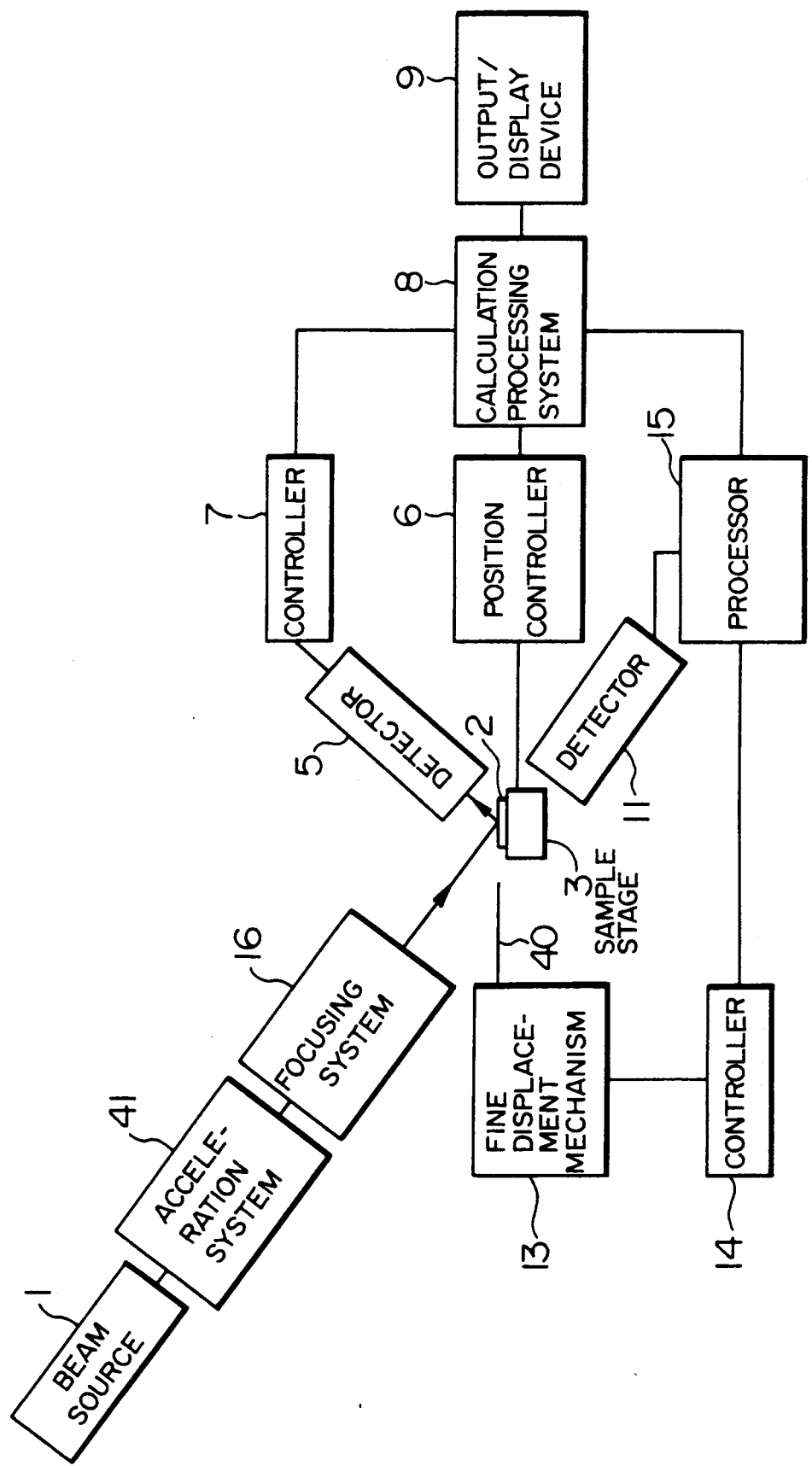

In the first to sixth embodiments, the probe beam is incident at right angles on the surface of the sample 2. In some cases, however, the angular distribution of particles emitted from the surface of the sample 2 is dependent on an angle, at which the probe beam is incident on the sample surface. In such cases, it is frequently preferable that the probe beam makes grazing incidence on the surface of the sample 2. Further, in a case where a probe beam reflected or scattered from the surface of the sample 2 is observed as in ion scattering spectroscopy (ISS) and electron energy loss spectroscopy (EELS), the grazing incidence is used. FIG. 7 shows the seventh embodiment of an apparatus for analyzing a surface in accordance with the present invention, in which embodiment the grazing incidence is used.

Referring to FIG. 7, the probe beam (or probe particles) emitted from the beam source 1 pass through the acceleration system 41 and the focusing system 16, and then impinge on the surface of the sample 7. As mentioned above, the grazing incidence is used in the present embodiment. The incident angle of the probe beam to the surface of the sample 2 is adjusted so that the detection of particles by the detector 5 is optimized. In a case where the acceleration system 41 and the focusing system 16 are useless, these systems can be removed.

The intensity distribution of the probe beam at the surface of the sample 2 is measured by using an aperture 40 attached to the fine displacement mechanism 13 and the detector 11. The aperture may be replaced by the knife edge used in the second embodiment, or a slit. The detector 11 is located so that the probe beam is incident at right angles on the detector. Other parts than the above-mentioned are the same as those of the first to sixth embodiments.

EMBODIMENT-8

Figure 8:
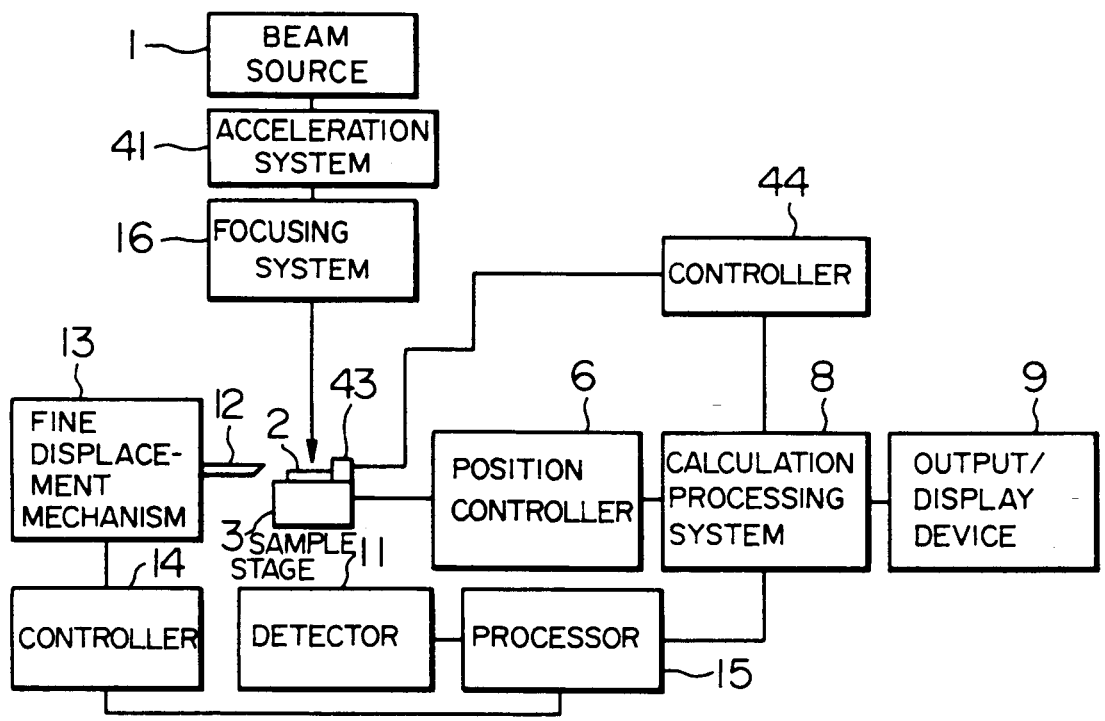

FIG. 8 shows the eighth embodiment of an apparatus for analyzing a surface in accordance with the present invention, in which embodiment a current or sound wave caused by irradiating the surface of the sample 2 with the probe beam is detected for surface analysis. As in the seventh embodiment, the acceleration system 41 and the focusing system 16 can be removed if these systems are useless.

Referring to FIG. 8, a current or sound wave caused by irradiating the surface of the sample 2 with the probe beam is detected by a sensor 43, and the output signal of the sensor 43 is supplied to a controller 44. While, a signal corresponding to the position of the probe beam on the surface of the sample 2 is supplied from the position controller 6 for controlling the fine displacement of the sample stage 3, to the high speed calculation processing system 8, which determines the function $S(X,Y)$ from the output signal of the position controller 6 and the output signal of the controller 44. Other parts than the above-mentioned are the same as those in the first to seventh embodiments.

In the sixth to eighth embodiments, the scanning operation of the probe beam of FIGS. 3 to 5 is not used. It is needless to say that in these embodiments, the scanning operation of the probe beam can be used in place of the fine displacement of the sample stage 3 or 35.

Further, a few methods of measuring the intensity profile of the probe beam have been used in the above-mentioned embodiments. It is to be noted that a method usable in one of the embodiments can be used in the remaining embodiments. That is, any method capable of measuring the intensity profile of the probe beam can be used in all of the embodiments, and the measurement of the intensity profile of the probe beam is essential to the embodiments.

EMBODIMENT-9

An example of the application of the present invention will finally explained. The above-mentioned embodiments are used for determining the distribution $n_A(x,y)$. However, the function $f(\eta,\theta)$ can be determined from the distribution $n_A(x,y)$ by using the equations (3) to (5). That is, in a case where a sample, in which the distribution $n_A(x,y)$ is known, for example, a metal mesh sample is irradiated with a probe beam, the intensity profile of the probe beam can be calculated from the known distribution $n_A(x,y)$, that is, it is possible to estimate the probe beam.

Figure 9:
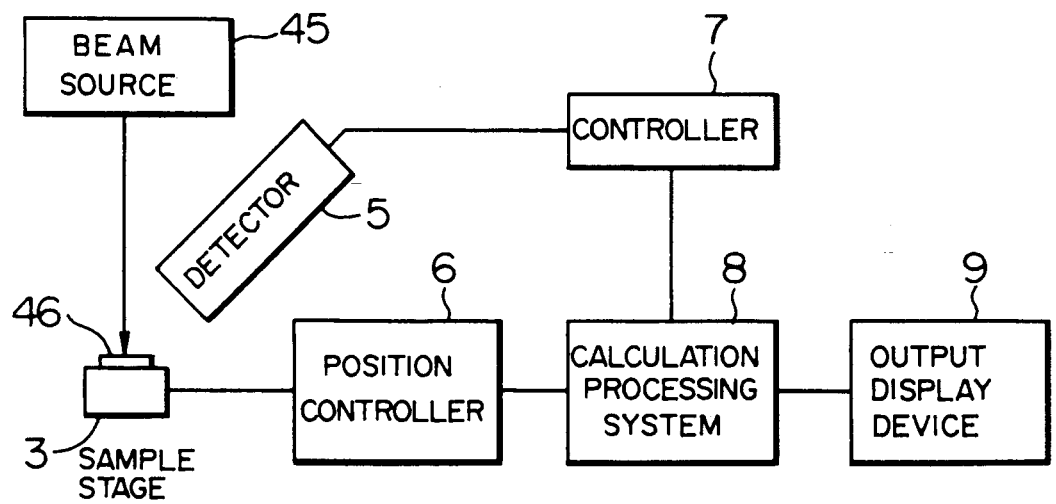
FIG. 9 is a block diagram showing an embodiment of an apparatus for finding the intensity profile of a probe beam in accordance with the present invention.

FIG. 9 shows an embodiment of an apparatus for determining the intensity profile of a beam in accordance with the present invention. Referring to FIG. 9, the probe beam emitted from a beam source 45 impinges on a sample 46. The beam source 45 emits the probe beam which is to be estimated. The probe beam may be focused, or may not be focused. As mentioned above, the sample 46 has known distribution $n_A(x,y)$, and may be, for example, a metal mesh.

As in the already explained embodiments, the high speed calculation processing system 8 determines the function $S(X,Y)$ from the observed signal which is delivered from the detector 5, and the output signal of the position controller 6. While, in the present embodiment the distribution $n_A(x,y)$ is known, and hence information on $n_A(x,y)$ can be previously loaded in the high speed calculation processing system to determine the function $N_A(X,Y)$ from the distribution $n_A(x,y)$ by using the equation (4). The function $\overline{F}(X,Y)$ can be calculated from the functions $S(X,Y)$ and $N_A(X,Y)$ by using the equation (3). Further, the intensity profile $f(\eta,\theta)$ can be calculated from the function $\overline{F}(X,Y)$ by carrying out the inverse transformation for the equation (5). All of these calculating operations are performed by the high speed calculation processing system 8, and the results of calculation are displayed on a display screen of the display means included in the calculation processing system 8. The results of calculation can be displayed on the display screen of the output/display device 9 in the form of a picture image, if necessary.

In the present embodiment, the probe beam is incident at right angles on the surface of the sample 46, and the emission from this surface is detected by the detector 5 to obtain the observed signal. The present embodiment may be modified so that the observed signal is obtained in a manner shown in one of FIGS. 6 to 8.

As is evident from the foregoing explanation, according to the present invention, the intensity profile of a probe beam and the signal distribution which is obtained by scanning a sample surface with the probe beam, are measured, and mathematical transformation is carried out for each of the intensity profile and the signal distribution to obtain the analytical result for the sample surface. When surface analysis is made in the above manner, the lateral resolution of the surface analysis is improved.

Thus, surface analysis according to the present invention is for superior in resolution and precision to conventional surface analysis, in which the lateral resolution is determined by the diameter of a probe beam.

We claim:

1. A method of analyzing a surface by using a probe beam, comprising the steps of:
   measuring the intensity profile of a probe beam at the surface of a sample;
   measuring the distribution of a detected signal along the surface of the sample by scanning the surface of the sample with the probe beam; and
   carrying out mathematic transformation for each of the intensity profile and the distribution of the detected signal.

2. A method of analyzing a surface as claimed in claim 1, wherein the probe beam is an electron beam.

3. A method of analyzing a surface as claimed in claim 1, wherein the probe beam is an ion beam.

4. A method of analyzing a surface as claimed in claim 1, wherein the probe beam is a neutral particle beam.

5. A method of analyzing a surface as claimed in claim 1, wherein the probe beam is a light beam.

6. A method of analyzing a surface as claimed in claim 1, wherein the probe beam are focused on the surface of the sample.

7. A method of analyzing surface as claimed in claim 6, wherein the detected signal is obtained by detecting electrons which are generated by irradiating the surface of the sample with the probe beam.

8. A method of analyzing a surface as claimed in claim 6, wherein the detected signal is obtained by detecting ions which are generated by irradiating the surface of the sample with the probe beam.

9. A method of analyzing a surface as claimed in claim 6, wherein the detected signal is obtained by detecting neutral particles which are generated by irradiating the surface of the sample with the probe beam.

10. A method of analyzing a surface as claimed in claim 6, wherein the detected signal is obtained by detecting light which is generated by irradiating the surface of the sample with the probe beam.

11. A method of analyzing a surface as claimed in claim 6, wherein the detected signal is obtained by detecting the probe beam which has passed through the sample.

12. A method of analyzing a surface as claimed in claim 6, wherein the detected signal is obtained by detecting the probe beam which has been reflected or scattered from the surface of the sample.

13. A method of analyzing a surface as claimed in claim 6, wherein the detected signal is obtained by detecting a current which is generated by irradiating the surface of the sample with the probe beam or by detecting a sound wave which is generated by irradiating the surface of the sample with the probe beam.

14. A method of analyzing a surface as claimed in claim 6, wherein the surface of the sample is scanned probe beam by moving the sample.

15. A method of analyzing a surface as claimed in claim 6, wherein the surface of the sample is scanned with the probe beam by deflecting the probe beam.

16. A method of analyzing a surface as claimed in claim 6, wherein the surface of the sample is scanned with the probe beam by changing a position where the probe beam is generated.

17. A method of analyzing a surface as claimed in claim 6, wherein the probe beam is directed to the surface of the sample so that grazing incidence is realized.

18. An apparatus for analyzing a surface, comprising:
means for generating a probe beam;
means for irradiating the surface of a sample with the probe beam;
means for measuring the intensity profile of the probe beam at the surface of the sample;
means for scanning the surface of the sample with the probe beam;
means for detecting a signal caused by irradiating the surface of the sample with the probe beam, and for measuring the distribution of the signal along the surface of the sample; and
means for carrying out mathematical transformation for each of the measured intensity profile and the measured signal distribution.

19. An apparatus for analyzing a surface as claimed in claim 18, wherein the probe beam is an electron beam.

20. An apparatus for analyzing a surface as claimed in claim 18, wherein the probe beam is an ion beam.

21. An apparatus for analyzing a surface as claimed in claim 18, wherein the probe beam is a neutral particle beam.

22. An apparatus for analyzing a surface as claimed in claim 18, wherein the probe beam is a light beam.

23. An apparatus for analyzing a surface as claimed in claim 18, further comprising means for focusing the probe beam on the surface of the sample.

24. An apparatus for analyzing a surface as claimed in claim 23, wherein the signal detection means detects electrons which are generated by irradiating the surface of the sample with the probe beam.

25. An apparatus for analyzing a surface as claimed in claim 23, wherein the signal detection means detects ions which are generated by irradiating the surface of the sample with the probe beam.

26. An apparatus for analyzing a surface as claimed in claim 23, wherein the signal detection means detects neutral particles which are generated by irradiating the surface of the sample with the probe beam.

27. An apparatus for analyzing a surface as claimed in claim 23, wherein the signal detection means detects light which is generated by irradiating the surface of the sample with the probe beam.

28. An apparatus for analyzing a surface as claimed in claim 23, wherein the signal detection means detects the probe beam which has passed through the sample.

29. An apparatus for analyzing a surface as claimed in claim 23, wherein the signal detection means detects the probe beam which has been reflected or scattered from the surface of the sample.

30. An apparatus for analyzing a surface as claimed in claim 23, wherein the signal detection means detects a current which is generated by irradiating the surface of the sample with the probe beam or detects a sound wave which is generated by irradiating the surface of the sample with the probe beam.

31. An apparatus for analyzing a surface as claimed in claim 23, wherein the surface of the sample is scanned with the probe beam by moving the sample.

32. An apparatus for analyzing a surface as claimed in claim 23, wherein the surface of the sample is scanned with the probe beam by deflecting the probe beam.

33. An apparatus for analyzing a surface as claimed in claim 23, wherein the surface of the sample is scanned with the probe beam by changing a position where the probe beam is generated.

34. An apparatus for analyzing a surface as claimed in claim 23, further comprising means for changing an angle, at which the probe beam is incident on the surface of the sample.

* * * * *